United States Patent
Heuer et al.

(10) Patent No.: US 10,251,677 B2
(45) Date of Patent: Apr. 9, 2019

(54) UNIPLANAR BONE ANCHORING ELEMENT

(71) Applicant: Silony Medical International AG, Frauenfeld Schweiz (CH)

(72) Inventors: Frank Heuer, Filderstadt (DE); Enrico Wirth, Donaueschingen (DE); Frank Trautwein, Filderstadt (DE)

(73) Assignee: SILONY MEDICAL INTERNATIONAL AG, Schweiz (CH)

( * ) Notice: Subject to any disclaimer, the term of this patent is extended or adjusted under 35 U.S.C. 154(b) by 0 days.

(21) Appl. No.: 15/577,254

(22) PCT Filed: Apr. 8, 2016

(86) PCT No.: PCT/EP2016/057810
§ 371 (c)(1),
(2) Date: Nov. 27, 2017

(87) PCT Pub. No.: WO2016/192877
PCT Pub. Date: Dec. 8, 2016

(65) Prior Publication Data
US 2018/0161072 A1    Jun. 14, 2018

(30) Foreign Application Priority Data
Jun. 1, 2015   (EP) ..................................... 15170172

(51) Int. Cl.
*A61B 17/70*    (2006.01)
(52) U.S. Cl.
CPC ...... *A61B 17/7038* (2013.01); *A61B 17/7032* (2013.01); *A61B 17/7037* (2013.01)
(58) Field of Classification Search
CPC ............ A61B 17/7038; A61B 17/7032; A61B 17/7037; A61B 17/7074; A61B 17/7076;
(Continued)

(56) References Cited

U.S. PATENT DOCUMENTS

| 8,986,349 B1* | 3/2015 | German | A61B 17/7068 606/279 |
| 2012/0016425 A1* | 1/2012 | Shaffrey | A61B 17/7032 606/305 |

(Continued)

FOREIGN PATENT DOCUMENTS

| EP | 1923011 A1 | 5/2008 |
| EP | 2198793 A2 | 6/2010 |

(Continued)

*Primary Examiner* — Pedro Philogene
(74) *Attorney, Agent, or Firm* — HM Law Group LLP; Vani Moodley, Esq.

(57) ABSTRACT

The invention relates to a uniplanar bone anchoring element (10) comprising an anchoring screw (12) with a bone thread (14) and a screw head (18), which is flattened on at least one side (17); a receiving element (20) that has a through-bore which tapers in a lower region (21) and in which the anchoring screw (12) can be received; and two limbs (25, 26) which extend upwards and which comprise a threaded profile (27) in an upper region, said threaded profile being designed for screwing on a securing screw. The receiving element (20) has an inner groove (24) which partly runs at least in the circumferential direction in the seat region of the anchoring screw head (18). The bone anchoring element also comprises a bearing element (40) for inserting into the inner groove (24) of the receiving element (20). The bearing element (40) is partly flattened on at least one side (47), and the groove and the bearing element are designed in a complementary manner such that the bearing element is positioned in the groove in a specified position.

6 Claims, 3 Drawing Sheets

(58) Field of Classification Search
CPC .............. A61B 17/7077; A61B 17/708; A61B 17/7083; A61B 17/7085; A61B 17/7086; A61B 17/7091; A61B 17/88; A61B 17/702; A61B 17/863; A61B 17/7005; A61B 17/7008; A61B 17/7082; A61B 17/864
USPC ................ 606/246–279, 86 A, 90, 104, 105; 403/326–330
See application file for complete search history.

(56) References Cited

U.S. PATENT DOCUMENTS

| | | | | |
|---|---|---|---|---|
| 2013/0023941 | A1* | 1/2013 | Jackson | A61B 17/7005 606/305 |
| 2014/0121703 | A1* | 5/2014 | Jackson | A61B 17/702 606/246 |

FOREIGN PATENT DOCUMENTS

| | | | |
|---|---|---|---|
| EP | 2198793 | A3 | 6/2010 |
| WO | 99/03415 | A1 | 1/1999 |

* cited by examiner

UNIPLANAR BONE ANCHORING ELEMENT

FIELD OF THE INVENTION

The invention relates to a uniplanar bone anchoring element and in particular a uniplanar pedicle screw, in which the screw shank is pivotable in only one plane.

STATE OF THE ART

Various bone anchoring elements, such as for example pedicle screws, are known in the state of the art. Such bone anchoring elements are used, for example, to correct vertebral malpositions in that these anchoring elements are screwed into the vertebra and are then connected to each other via transverse rods in order to correct the malpositions and fix them in the correct position. Such anchoring elements can be designed as monoaxial screws in which the screw shank is fixedly connected to the receiving element for the transverse rod and in which the alignment of the receiving element is therefore fixed in relation to the longitudinal axis of the screw shank. Another embodiment is designed as a polyaxial screw in which the bone screw, which is screwed into the vertebra, is pivotable in any desired direction in relation to the receiving element.

However, it may be the case that pivotability in only one plane is desired. This is the case, for example, in derotation manoeuvres in the care of scoliotic spines. EP 1 923 011 therefore proposes a system in which two lateral through-bores are made in a receiving element, into which two pins can be inserted, against which two flat surfaces then abut against the screw head. Through the flat surfaces at the screw head, in co-operation with the two pins at the sides, it is ensured that the shank with the bone thread can only pivot in one plane. However, it is problematic here that the pins only strike the flat surfaces of the screw with a rounded side and a very high degree of precision is therefore required during the production of the pins and the pin bores. Since even in the case of low tolerances, the pin can lose the linear contact with the flat surface at the screw head and thereby not maintain the linear contact between pin and surface, which can lead to a pivotability outside of the desired plane. Furthermore, a certain degree of caution is also necessary during surgical insertion of the bone anchoring element so that the pins do not fall out of the through-bores of the anchoring element.

PRESENTATION OF THE INVENTION

The object of the present invention is therefore to provide a uniplanar bone anchoring element which is simple to produce and safe to handle. This is provided for by a bone anchoring element with the features of claim 1.

A uniplanar bone anchoring element according to the invention comprises an anchoring screw with a bone thread and a screw head, wherein the screw head is flattened on at least one side, a receiving element, wherein the receiving element has a through-bore which tapers in a lower region and in which the anchoring screw can be received, and two limbs which extend upwards and have a threaded profile in an upper region, which threaded profile is designed for screwing on a securing screw, wherein the receiving element has an inner groove which runs at least partly in the circumferential direction in the seat region of the anchoring screw head and a bearing element for inserting into the inner groove of the receiving element, wherein the bearing element is partly flattened on at least one side, wherein the groove and the bearing element are designed, in particular in a complementary manner, such that the bearing element is positioned in the groove in a predetermined position. The predetermined position defines not only the circumferential direction, which is preferably defined by the two end walls of the groove, but also the position of the flattened side of the bearing element, which is to be directed towards the screw head. It is thereby provided that the flattened side of the bearing element bears against the flattened side of the screw head, since the bearing element cannot turn in the groove.

The respective ends preferably level off in the circumferential direction. This means that the ends do not terminate abruptly but the base of the groove rises continuously until the groove is no longer present. This groove ramp preferably has a length of at most 7 mm, preferably 5 mm and further preferably 3 mm. The ramp is preferably at least 0.5 mm to 1 mm long. Such a ramp has the advantage that it is simple to produce but at the same time prevents the bearing element in the groove in the assembled state from slipping in the groove due to the already slight rise at the start of the ramp.

The inner groove extends in the circumferential direction, preferably over half of the circumference, further preferably over three quarters of the circumference. However, the circumferential groove and the bearing element are designed at least semi-circular in circumference and have the advantage that the position of the bearing element is then defined in every direction. As soon as the bearing element is inserted in a semi-circular groove, it can no longer fall out even without a screw inserted into the receiving element.

Furthermore, in a preferred embodiment, the cross section of the groove and the bearing element can define the predetermined position. For example, a perpendicular surface can be provided in the groove and an additional complementary perpendicular surface can be provided on the bearing element so that the bearing element can only sit in the groove in one position. Likewise, possible is an oval cross section or any other shape which makes it possible for the bearing element to be inserted into the groove in only one position. The base of the groove is preferably designed as a flat surface so that the bearing element can align itself on the base of the groove with a corresponding surface. The inner groove and in particular the base of the groove can be designed curved in the circumferential direction, but can also run straight. In the case of a U-shaped bearing element with straight limbs, these can prevent the bearing element from slipping in the groove in the circumferential direction. Accordingly, the bearing element can be designed as a partially circular bracket.

The inner groove is preferably formed below the limbs of the receiving element. It is thereby ensured that the flat bearing surfaces of the screw head and of the bearing element are not adversely affected by the arrangement of other components of the bone anchoring element.

The bearing element is preferably designed annular, further preferably U-shaped with two substantially parallel limbs with the result that the screw head can be received between these parallel limbs. Furthermore, the bearing element is preferably designed with a substantially rectangular cross section, which makes it easier for the surfaces between groove and bearing element and between bearing element and screw head to bear against each other. The edges of the groove and of the bearing element are preferably also provided with radii which, however, does not adversely affect the contact and the secure seating between the individual parts.

Furthermore, the anchoring screw has flattened points on two substantially opposite sides with the result that the screw can come into contact with a bearing element on both sides. This embodiment is used in particular with the U-shaped bearing element.

BRIEF DESCRIPTION OF THE DRAWINGS

FIG. 1b shows an exploded view of the uniplanar bone anchoring element from FIG. 1a;

FIG. 2a shows a longitudinal section of an assembled uniplanar bone anchoring element according to the present invention;

FIG. 2b shows the individual parts of an assembled uniplanar bone anchoring element from FIG. 2a.

DESCRIPTION OF THE PREFERRED EMBODIMENTS

Figures 2A, 2B:
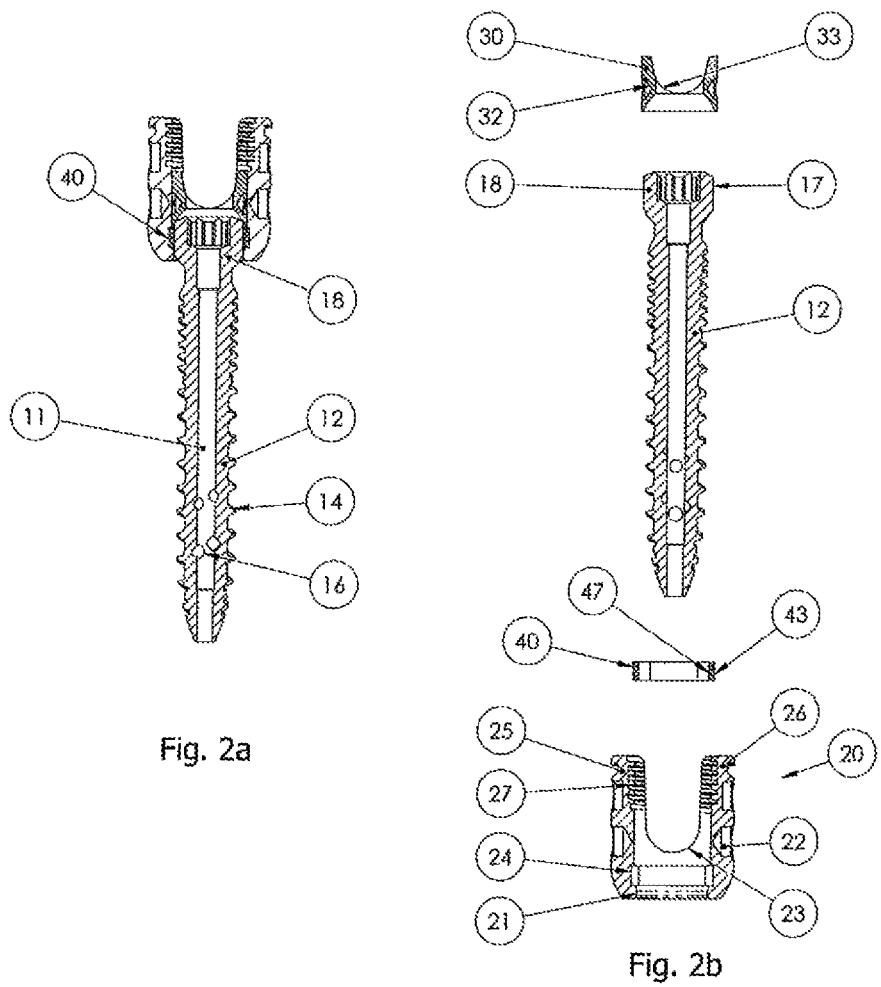
Figure 3:
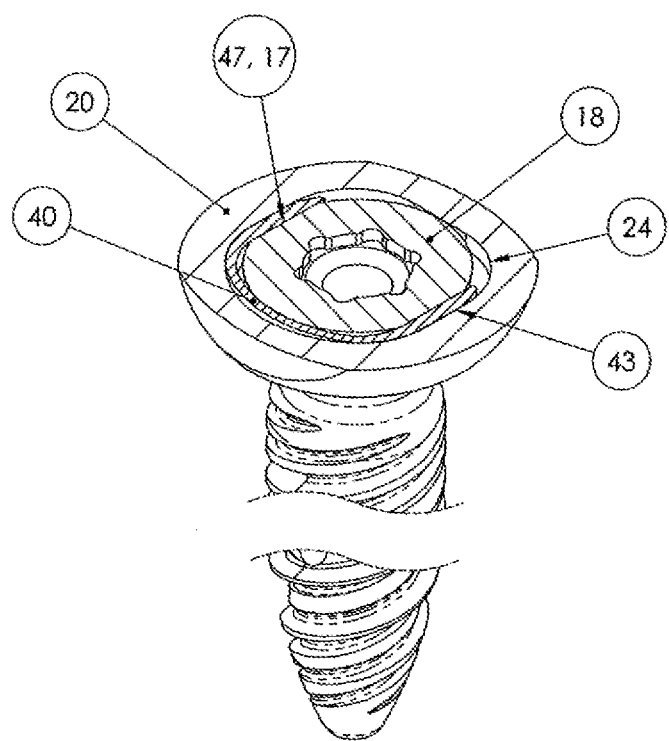
FIG. 3 shows a section through the receiving element at the upper end of the inner groove as well as the seating of a U-shaped bearing element on the screw head.

When top and bottom are mentioned in the following, reference is being made to an arrangement which can be seen in FIG. 2a. The upper end of the uniplanar screw thus relates to the upper end of the mating part with the thread, while the lower end relates to the tip of the screw shank. Furthermore, by axial direction is meant the axial direction of the bone anchoring element from FIG. 2a, the radial direction is perpendicular to the axial direction and a circumferential direction refers to a direction around the axial direction.

Figure 1A:
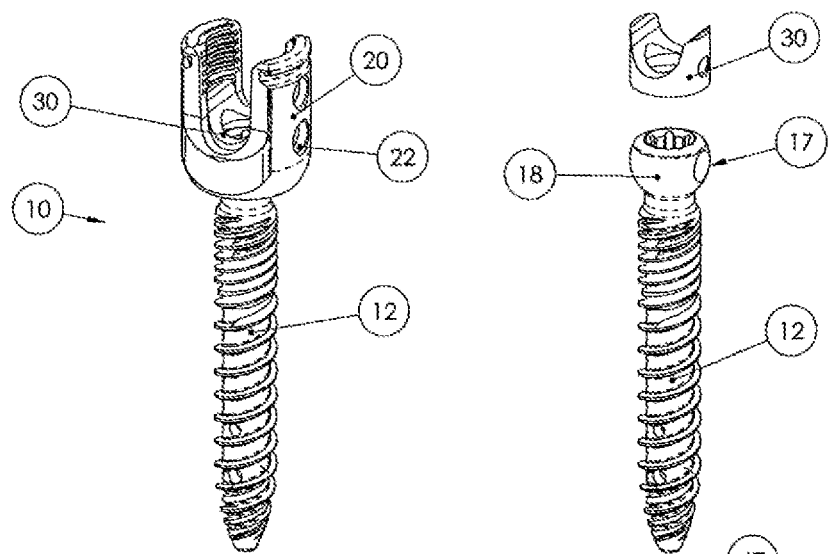
FIG. 1a shows an isometric view of an assembled uniplanar bone anchoring element according to the present invention.
Figure 1B:
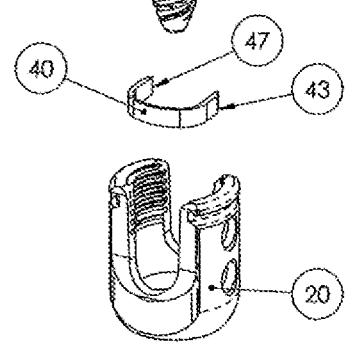

In FIG. 1a, an isometric view of the bone anchoring element 10 according to the invention can be seen. In the present case, the bone anchoring element 10 comprises a screw 12, which is anchored in the bone, a receiving element 20 for receiving the screw 12 and a transverse rod (not shown), a pressure piece 30, with which the screw 12 is mounted in the receiving element 20, and the bearing element 40. The screw 12 consists of a screw shank and a screw head 18. Arranged on the screw shank is a bone thread 14 which can be designed at least partly with multiple threads. The screw can have a through-bore 11 which can comprise openings 16 in the screw shank in the lower region. With these holes 16, a screw screwed into the bone can be secured in the bone with bone cement, in that the bone cement is applied to the lower end of the screw 12 through the bore. A flattened region 17 is provided on the screw head 18 on at least one side. Preferably, and as shown in the figures, this flattened region 17 is provided on two substantially opposite sides of the screw head 18. In principle, more than two opposite flattenings can also be provided, for example four flattened regions which are each offset with respect to each other by 90°, or also eight, which are then each offset with respect to each other by 45°. Such a screw has several end positions in which the flattened regions on the screw head can co-operate with the flattened regions on the bearing element.

The pressure piece 30, which is inserted in the receiving element 20, serves to hold the screw in the receiving element 20. For this, in the assembled bone anchoring element, as can be seen in FIG. 1a, a pressing force is applied in the bore 22 which in turn applies a force in the bore 32 of the pressure piece 30 and thus compress the pressure piece above the screw. Although the screw 12 can thereby still be pivoted, it can no longer fall out of the receiving element since the region of the bore 22 is squeezed into the pressure piece 30. The pressure piece 30 has a depression 33 in which the transverse rod is placed later.

The receiving element 20 has a through-bore with a tapering lower end 21. The lower part of the screw head 18 is mounted in this tapering lower end 21. The receiving element 20 furthermore has the bores 22 mentioned above for compressing the pressure piece and two limbs 25, 26 which extend upwards and comprise an internal thread 27. Later, a pressure screw, which presses on the transverse rod, is screwed into the internal thread 27 and thus fixes all of the components of the bone anchoring element. In the present case, this thread is shown as an internal thread, but it is also possible without problems to realize this as an external thread and not to use a grub screw as pressure screw but rather a screw nut.

The receiving element 20 has a seat 23 for the transverse rod which is designed as a U-shaped recess. The transverse rod is then placed in this recess and the securing screws (here a grub screw) are screwed into the thread 27. In a lower region of the receiving element 20, preferably below the limbs 26, 25, a groove 24 is provided into which the bearing element 40 is inserted. The groove preferably also has flat surfaces. The groove preferably runs circumferentially and corresponds substantially to the shape of the bearing element 40, both in the circumferential direction and in cross section. If the bearing element 40 is designed as a ring or partially circular ring, the cross section of the groove is unimportant since the positions of the bearing surfaces 47 for the flattened regions 17 of the screw head are held in position by the annular shape. However, if the bearing element is not designed at least semi-circular, it is advantageous, in particular in the case of shorter bearing elements which are inserted on only one side of the receiving element, if the positioning of the flat bearing surface is effected via the cross section of the bearing element and of the groove. For this purpose, a substantially square or rectangular cross section is preferably suitable, but it can just as well be an oval cross section or another shape which can provide a predetermined position of the bearing element 40 in the groove.

The bearing element 40 is preferably designed as a ring with at least one slot or a partial ring so that the bearing element 40 can be compressed resiliently and can be inserted into the groove of the receiving element 20. However, this can also be made possible, e.g., by changing the material or the material property (e.g. the thickness). Thus, a closed ring can also be compressed sufficiently that it can be inserted into the inner groove. The insertion can be effected from above or from below. If the bearing element 40 is designed annular, it can no longer fall out of the circumferential groove.

So that the bearing element 40 can also not turn in the groove in the circumferential direction of the receiving element, the groove in the receiving element 20 is preferably also not realized over the whole circumference but only corresponding to the dimensions of the bearing element 40. Here, the bearing element 40 preferably also has a further flat surface 43 which co-operates with the flat base of the groove 24 in the receiving element 20.

In particular, the bearing element 40 is preferably designed U-shaped, with the result that the two substantially parallel limbs of the "U" can likewise prevent the turning of the bearing element 40 in the groove 24 in the event that the groove 24 is actually formed over the whole circumference in the receiving element 20. Through these two substantially parallel limbs and their perpendicular outer surfaces 43, the bearing element 40 can no longer turn in the groove 24 in the circumferential direction.

In principle, however, the bearing element 40 can also be designed as a simple pin (straight or bent). The bearing element 40 has at least one flattened side 47 which cooperates with the flattened region 17 of the screw head 18 and ensures pivoting exclusively in a desired plane of the bone screw. Due to the fact that the bearing element also bears extensively against the flat region of the screw head, pivoting in planes other than the desired one is also not possible in the case of smaller degrees of inaccuracy.

The invention claimed is:

1. A uniplanar bone anchoring element (10), comprising:
an anchoring screw (12) with a bone thread (14) and a screw head (18), wherein the screw head is flattened on at least one side (17);
a receiving element (20), wherein the receiving element has a through-bore which tapers in a lower region (21) and in which the anchoring screw (12) is received, and two limbs (25, 26) which extend upwards and have a threaded profile (27) in an upper region, wherein the threaded profile (27) is designed for screwing on a securing screw, wherein the receiving element (20) has an inner groove (24) which runs at least partly in the circumferential direction in seat region of the anchoring screw head (18); and
a U-shaped bearing element (40) for inserting into the inner groove (24) of the receiving element (20), wherein the U-shaped bearing element (40) is partly flattened on at least one side (47) so as to be inserted in the inner groove (24) of the receiving element (20) and to contact the flattened side of the anchoring screw head (17) so as to allow the anchoring screw (12) to be pivoted in only one plane;
wherein
the inner groove (24) and the U-shaped bearing element (40) are designed in a complementary manner such that the U-shaped bearing element (40) is positioned in the groove in a predetermined position and the U-shaped bearing element (40) includes two substantially parallel limbs; and
wherein the inner groove (24) and the U-shaped bearing element (40) are designed with a substantially rectangular cross section.

2. The bone anchoring element (10) according to claim 1, in which the ends of the inner groove (24) level out in the circumferential direction.

3. The bone anchoring element (10) according to claim 1, in which the inner groove (24) extends circumferentially in the receiving element (20) and the U-shaped bearing element (40) is designed as a partially circular bracket or ring.

4. The bone anchoring element (10) according to claim 1, in which the cross sections of the groove (24) and of the U-shaped bearing element (40) define the predetermined position.

5. The bone anchoring element (10) according to claim 1, in which the inner groove (24) is formed below the limbs (25, 26) of the receiving element.

6. The bone anchoring element (10) according to claim 1, in which the anchoring screw (12) is flattened on two substantially opposite sides.

* * * * *